United States Patent [19]

Kramer et al.

[11] Patent Number: 5,407,163
[45] Date of Patent: Apr. 18, 1995

[54] SLIDING IV POLE

[75] Inventors: Kenneth L. Kramer, Greensburg; Matthew W. Weismiller, Batesville, both of Ind.

[73] Assignee: Hill-Rom Company, Inc., Batesville, Ind.

[21] Appl. No.: 154,963

[22] Filed: Nov. 19, 1993

[51] Int. Cl.6 .............................................. E04G 3/00
[52] U.S. Cl. ..................................... 248/291; 5/503.1; 5/658; 248/298
[58] Field of Search ............ 248/291, 298, 308, 311.3, 248/284, 286; 5/503.1, 658, 662, 600

[56] References Cited

U.S. PATENT DOCUMENTS

| 1,290,809 | 1/1919 | Truax . | |
|---|---|---|---|
| 2,470,524 | 5/1949 | Scudder . | |
| 2,673,771 | 2/1952 | Krewson . | |
| 2,696,963 | 12/1954 | Shepherd | 248/229 |
| 4,113,222 | 9/1978 | Frinzel | 248/412 |
| 4,262,872 | 4/1981 | Kodet | 248/311.3 |
| 4,905,944 | 3/1990 | Jost et al. | 248/125 |
| 5,094,418 | 3/1992 | McBarnes, Jr. et al. | 248/286 |
| 5,125,607 | 6/1992 | Pryor | 248/125 |

Primary Examiner—Ramon O. Ramirez
Attorney, Agent, or Firm—Wood, Herron & Evans

[57] ABSTRACT

A pole support for an IV pole mounted adjacent a patient support and having two pole supports separated by a pair of tracks providing guided paths between the two pole supports. The IV pole has a pole locking block at one end with pins that engage the tracks for slidingly moving the IV pole along the track between the two pole supports. The pins on the pole locking blocks further engage first slots and notches in the two pole supports for supporting the IV pole in a generally vertical position; and the pins engage second slots and notches in the two pole supports for supporting the IV pole in a generally horizontal position.

18 Claims, 2 Drawing Sheets

SLIDING IV POLE

BACKGROUND OF THE INVENTION

1. Field of the Invention

The present invention relates generally to the area of IV pole assemblies and, more particularly, to a sliding IV pole assembly for use with a patient support in which the IV pole may be slidably transferred between two locations with respect the patient support and secured in a vertical position at each of the two locations.

2. Description of Related Art

Medical patients often require intravenous equipment which typically is supported by a vertical pole located in the proximity of the patient. If the patient is on a patient support such as a hospital bed, the vertical support pole for the intravenous equipment may be attached to the bed as shown in U.S. Pat. No. 2,673,771. Alternatively, the intervenous equipment may be free standing on a stationary but portable base or a wheeled base as shown in U.S. Pat. No. 4,905,944. When the intravenous equipment is supported by a free-standing base, an extra attendant is required to independently move the intravenous equipment when moving the bed and patient. There are constructions such as that shown in U.S. Pat. No. 5,094,418 that permit a bed mounted pole to be moved with the bed and stored in a horizontal position for transportation or storage. Intravenous equipment mounted on the bed itself is transportable with the bed; however, it is difficult and time consuming to detach the pole and associated intervenous equipment and reattach it at another location or position with respect to the bed.

The above designs have the disadvantages of either requiring extra manpower to independently look after the intravenous equipment during transportation or requiring extra time in moving the equipment from one location to another with respect to the patient in the bed.

SUMMARY OF THE INVENTION

To overcome the disadvantages of the above described mechanisms, the present invention provides a pole support for intravenous equipment which is mounted on a patient support, such as a bed, stretcher or chair, and may be easily and quickly slidingly moved between two locations on the patient support and supported in a vertical position at each of those locations. In addition, the present invention permits the pole support to be moved to a generally horizontal position for storage. Therefore, the invention is particularly useful in intensive care and other emergency care facilities in which the patient's intravenous needs are substantial, and attendants need to quickly switch the location of the intravenous equipment.

According to the principles of the present invention and in accordance with the described embodiments, a patient support has a pair of pole supports connected at two locations. A guide member is connected between the pair of pole supports and provides parallel tracks between the two locations. An intravenous ("IV") pole has a locking block at one end with pins engaging the parallel tracks of the guide member, thereby permitting the IV pole to be selectively slidably moved along the guide member between the two locations. Each of the mounting brackets includes tapered slots for receiving the pins on the locking block thereby supporting the IV pole in a vertical position at the two locations. Further, each of the mounting brackets includes other slots for engaging the pins on the locking block to support the IV pole in a generally horizontal position.

The present invention has the advantage of permitting an attendant to quickly move the IV pole and associated intravenous equipment from one side of the patient support to the other. Further, the IV pole may be collapsed and moved to a generally horizontal position to prevent interference when the patient support is transported to a different location or placed in storage.

These and other objects and advantages of the present invention will become more readily apparent during the following detailed description in conjunction with the drawings herein.

DETAILED DESCRIPTION OF THE INVENTION

Figure 1:
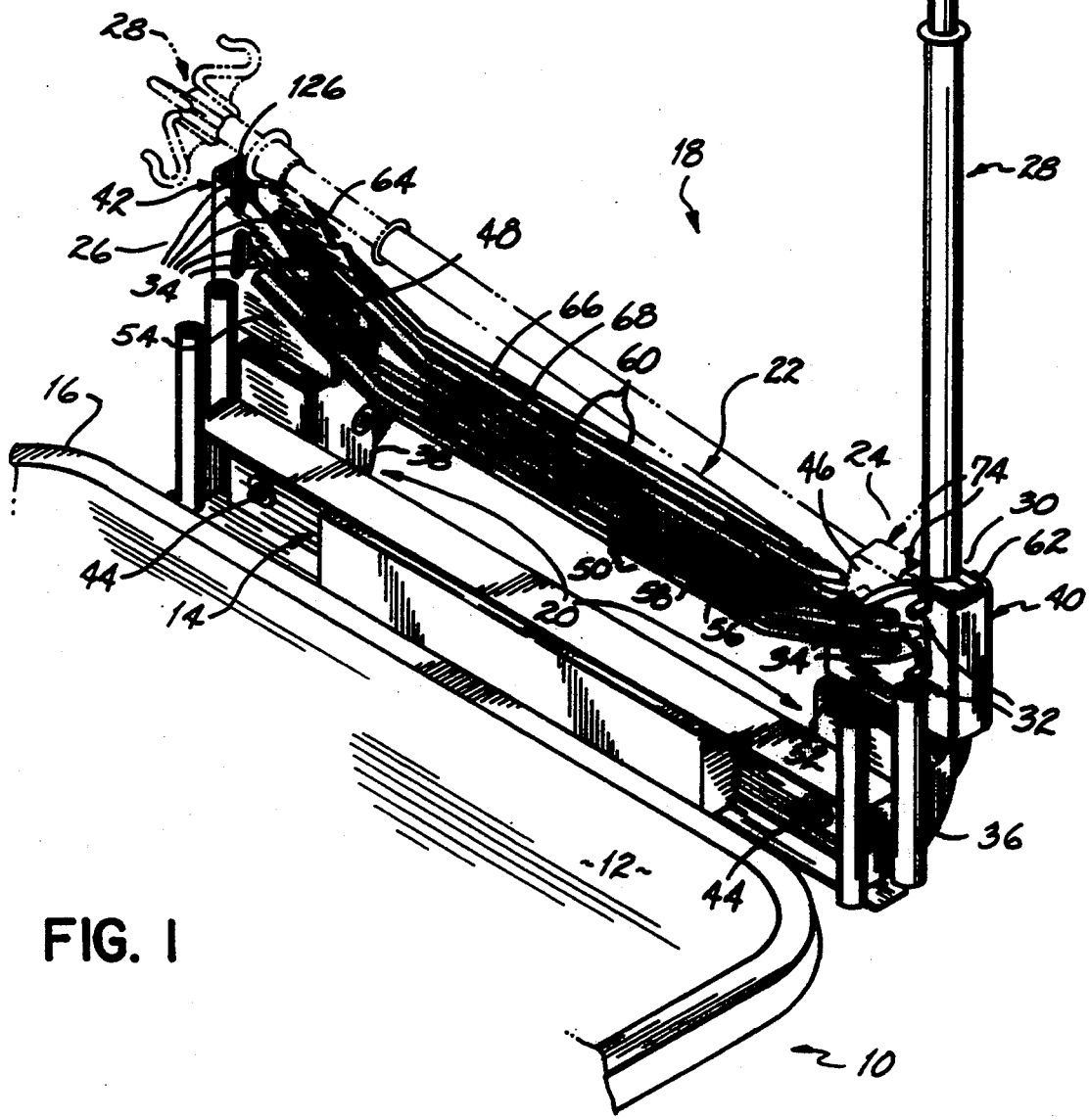
FIG. 1 is a perspective view of the sliding IV pole assembly of the present invention with the IV pole shown in the operative and stored positions.
Figures 2, 3:
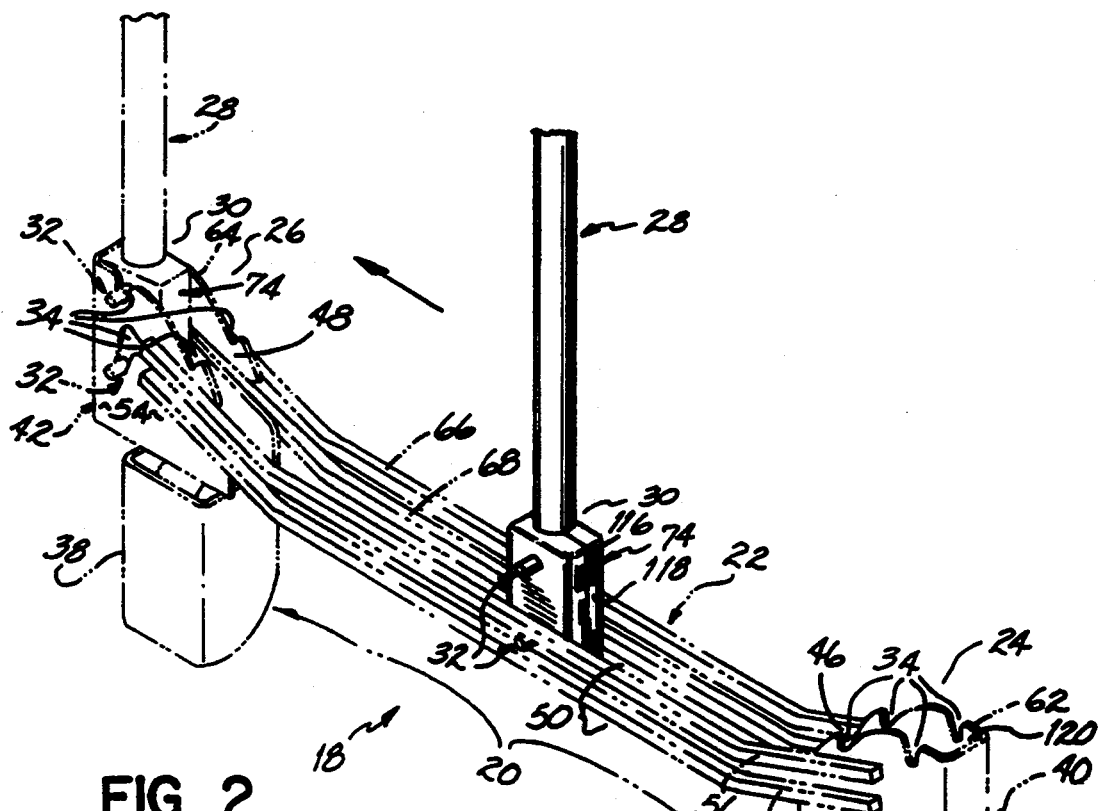
FIG. 2 is a partial perspective view, illustrating the sliding motion of the IV pole between two locations relative to a patient support.
FIG. 3 is a disassembled perspective view of the pole support engaging the guide member at one end.

Referring to FIG. 1, a patient support device, such as, for example, a hospital bed 10, includes a patient support structure 12 and a head frame structure 14 which is rigidly connected to one end 16 of the patient support structure 12. The sliding IV pole assembly 18 is connected to the hospital bed 10 by means of a pole support base 20. A guide member 22 is connected to the base 20 to provide a track between a first location 24 and a second location 26 relative to the bed 10. An IV pole 28 has one end 30 engaging the guide member 22. The IV pole further has locking pins 32 which engage notches 34 on the base 20 for releasably supporting the IV pole 28 in a generally vertical position. To move the pole between the locations 24, 26, the pole 28 is lifted vertically to release the locking pins 32 from notches 34; and the locking pins 32 are moved into contact with the guide member 22. As shown in FIG. 2, the IV pole 28 may then be slid across the guide member 22 to the second location 26. The locking pins 32 are engaged in corresponding notches 34 in the pole support base 20 at the second location 26 thereby supporting the pole in a generally vertical position at the second location 26. In addition, if the pole is at the first location 24, the IV pole 28 may be lifted vertically to lift the locking pins 32 from the notches 34 and the IV pole 28 may be rotated to a generally horizontal position as shown in phantom in FIG. 1.

Referring to the construction in more detail, the pole support base 20 includes of a pair of mounting brackets 36, 38 attached to the head frame structure 14 of the patient support structure 12 at the first and second locations 24, 26, respectively. Further, the base includes pole locking brackets 40, 42 which function as receptacles for the poles, or pole supports, and are connected to the mounting brackets 36, 38 respectively. Each of the mounting brackets 36, 38 is made from a U-channel piece, the base of which is bolted to the head frame structure 14 by fasteners 44. Each of the pole locking brackets, 40, 42 is a U-channel member which is welded or otherwise rigidly connected to a respective mounting bracket 36, 38. The U-channel pole supports 40, 42 are mounted so that the open ends 46, 48 are directed inwardly relative to the bed 10 and facing each other. The guide member 22 includes a pair of first tracks 50 connected to one side 52, 54 of the respective U-channel pole supports 40, 42. The pair of first tracks 50 has an upper rail 56 and lower rail 58. The guide member 22 further includes a pair of second tracks 60 extending between and connected to the opposing sides 62, 64 of the respective U-channel pole supports 40, 42. The pair of second tracks 60 include an upper rail 66 and a lower rail 68. The first and second tracks 50, 60 of the guide member 22 extending between the first and second locations 24, 26 provide guided paths 70, 72 for the moveable IV pole 28.

Figure 4:
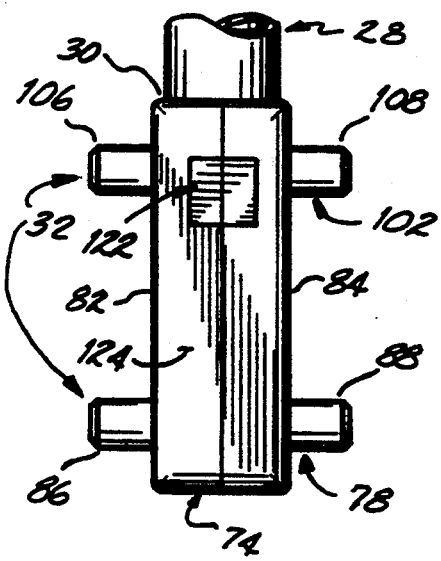
FIG. 4 is an end view of the locking block at one end of the pole.

FIGS. 3 and 4 illustrate the details of the construction of the pole locking bracket 40 which is identical to the construction of the opposing pole locking bracket 42. A member such as pole locking block 74 is connected to one end 30 of the IV pole 28. The locking block 74 is dimensioned and sized to fit between the sides 52, 62 of the pole locking bracket 40. The pole locking block 74 includes a first rod 78 which is inserted in a bore 80 through the locking block 74. The opposed ends 86, 88 of the first rod 78 project from the respective sides 82, 84 of the locking block 74 to form a first pair of the pins 32.

Each side 52, 62 of the pole locking bracket 40 has a first slot 90 which is generally horizontal and located between the upper and lower rails 56, 58 of the first track 50. The first slots 90 and the guided paths 70, 72 in the tracks 50, 60 are sized to receive the first pins 86, 88, respectively. The first slots 90 are contiguous with and provide an extension of the guided paths 70, 72 of the first and second tracks 50, 60. Each side, 52, 62 of the pole locking bracket 40 further includes a generally vertical second slot 94 intersecting an opposite end 96 of the first slot 90. Each of the second slots 94 have one end 98 extending upward in a generally vertical direction beyond and above the other end 96 of the first slot 90. Each of the second slots 94 has an opposite end 100 extending downward in a generally vertical direction past and below the other end 96 of the first slots 90. The first and second slots 90 and 94 are generally oriented to form a right angle therebetween. The opposite end 100 of each of the second slots 94 is tapered in width to a dimension slightly less than the diameter of the ends 86, 88 of the first rod 78.

A second rod 102 is inserted in bore 104 of locking block 74, and the ends 106, 108 of the rod 102 extend from the respective sides 82, 84 of the locking block 74 to form a second pair of the pins 32. The rod 102 projects beyond the sides 82, 84 to form a pair of second pins 106, 108. Each side 52, 62 of the pole locking bracket 40 has a first notch 110 in an upper peripheral edge 112. The first notches 110 are dimensioned and sized to receive the pair of second pins 106, 108. The upper peripheral edge 112 on each side 52, 62 of the pole locking bracket 40 contains second notches 114 which are also dimensioned in size to receive the second pins 106, 108.

Referring to FIGS. 1 and 2, to better secure the pole 28 in a vertical position, a wedge shaped member 116 is molded onto one end 118 of the locking block 74. When the locking block 74 is inserted in the pole locking bracket 40, the pins 32 engage the slots 94 and first notches 110 on the sides 52, 62 of the pole locking bracket 40 at the first location 24. In addition, the wedge shaped member 116 engages an interior surface of the closed end 120 of the pole locking bracket 40. The wedge shaped member 116 is operative to push the pins 32 on the pole locking block 74 against the sides of the slots 94 and first notches 11 0, thereby better securing the IV pole more tightly in a vertical orientation. In a similar manner, as shown in FIGS. 1 and 4, a wedge shaped member 122 is molded onto the opposite end 124 of the pole locking block 74. When the IV pole 25 is moved to the second location 26, and the pole locking block is inserted into the pole locking bracket 42, the wedge shaped member 122 engages an interior surface of a closed end 126 of pole locking block 42, thereby better securing the IV pole 25 in a vertical position.

In use, the IV pole 28 is vertically supported at the first location 24 by the pair of first pins 86, 88 engaging ends 100 of the slots 94 in the pole locking bracket 40. In addition, the pair of second pins 106, 108 are located in first notches 110. The U-channel pole support 40 captures the sides 82, 84 of the pole locking block 74 thereby supporting the IV pole 28 in a generally vertical plane. The engagement of the first pins 86, 88 into tapered ends 100 of slots 94, and the engagement of second pins 106, 108 into first notches 110 prevents rotation of the pole within the generally vertical plane defined by the sides 52, 62 of the pole locking bracket 40. To move the pole from one location to another, the pole is manually lifted vertically upward to disengage first pins 86, 88 from the ends of slots 94 and second pins 106, 108 from first notches 110 and moving the first pins 86, 88 into the slots 90 and along the guided paths, 70, 72 into the pole locking bracket 42 at the second location 26. At the second location, the first pins 86, 88 are moved with the pole locking bracket 42 by moving through the first slots 90 into the second slots 94 and lock into the tapered lower ends 100 of the slots 94 in pole locking bracket 42. Simultaneously, the second pins 106, 108 are moved along the curved peripheral edge 112 into notches 110. Therefore, the IV pole and associated intervenous equipment can be easily and quickly moved from one side of the bed to the other.

When not in use, the IV pole 28 may be lifted vertically upward to disengage first pins 86, 88 from the tapered ends 100 of second slots 94 and to disengage second pins 106, 108 from first notches 110. The IV pole is then rotated approximately 90 degrees with respect to the first pins 86, 88 thereby moving the IV pole to a generally horizontal position. The IV pole is supported in the generally horizontal position by the first pins 86, 88 engaging the ends 98 of second slots 94 and the second pins 106, 108 engaging the second notches 114 on the upper peripheral edge 112 of the respective pole support 40, 42.

While the present invention has been set forth by a description of the embodiment in considerable detail, it is not intended to restrict or in any way limit the claims to such detail. Additional advantages and modifications will readily appear to those who are skilled in the art. For example, the pole support base 20 can be comprised of a single mounting bracket extending between the pole supports 40, 42. Alternatively, the base 20 may be centrally located and attached to the tracks 50, 60. The base 20 may be rigidly connected or removably mounted to the head frame support of the bed 10. The IV pole 28 may be rotatably or nonrotatably mounted within the locking block 74. Instead of being formed from a common rod, the pins 86, 88 may be separate pieces and may be separately connected to the locking block 74. The IV assembly of the present invention may be applied to other patient supports such as a stretcher, a stationary chair or wheel chair. Further, the structure of the present invention may be free-standing and supported on its own independent stationary or wheeled base independent of the patient support. The invention in its broadest aspects is therefore not limited to the specific details shown and described. Accordingly, departures may be made from such details without departing from the spirit and scope of the invention.

What is claimed is:

1. An IV pole assembly movable between at least two locations comprising:
   an IV pole;
   a base for supporting the IV pole in a generally vertical position at each of the two locations;
   a guide connected to the base to provide a track between the two locations relative to the base; and
   a member connected to the IV pole for engaging the guide to cause the IV pole to follow the track when moving the IV pole between the two locations.

2. The IV pole assembly of claim 1 wherein the base further supports the IV pole in a generally horizontal position at one of the two locations.

3. The IV pole assembly of claim 1 wherein the base further includes a receptacle connected to the base at each of the two locations for supporting the IV pole in the generally vertical position at each of the two locations.

4. The IV pole assembly of claim 3 wherein the guide includes two pair of rails connected between the receptacles wherein a track between the two locations is formed between each of the pair of rails.

5. The IV pole assembly of claim 4 wherein the member connected to the IV pole includes two pins, each of the pins engaging one of the pair of rails.

6. The IV pole assembly of claim 5 wherein the receptacles are U-shaped pole locking brackets.

7. The IV pole assembly of claim 6 wherein each of the U-shaped pole locking brackets includes generally horizontal first slots in opposed sides of each of the U-shaped pole locking brackets, and each of the U-shaped pole locking brackets is connected to ends of the two pair of rails so that first ends of each of the first slots are contiguous with and form extensions of the tracks between the two pair of rails.

8. The IV pole assembly of claim 7 wherein the member connected to the IV pole includes a pole locking block connected proximate one end of the IV pole and slidably engagable in the U-shaped pole locking brackets.

9. The IV pole assembly of claim 8 wherein the pole locking block includes a pair of first pins extending from opposite sides of the pole locking block and engagable with the first slots, thereby permitting the IV pole and pole locking block to slide in the first slots and the tracks between the U-shaped pole locking brackets at the two locations.

10. The IV pole assembly of claim 9 wherein the pole locking brackets further include a pair of generally vertical second slots located at an opposite end of each of the first slots and intersecting each of the first slots to extend slightly above and below the first slots, the pair of second slots having upper ends and tapered lower ends.

11. The IV pole assembly of claim 10 wherein the pole locking block further includes a pair of second pins, the pair of second slots receiving the pair of first pins in the tapered lower ends to lock the IV pole in a generally vertical position, and the pair of second slots receiving the pair of second pins in the upper ends to lock the IV pole in a generally horizontal position.

12. The IV pole assembly of claim 11 wherein the pair of pole locking brackets further include:
    a pair of first notches on peripheral edges of the open sides for receiving the pair of second pins to further support the IV pole in the generally vertical position, and
    a pair of second notches on peripheral edges of the open sides and displaced below the pair of first notches for receiving the pair of second pins to further support the IV pole in its generally horizontal position.

13. A patient support device having a movable IV pole assembly associated with one side of the patient support device comprising:
    a base associated with the one side of the patient support device;
    a guide connected to the base to provide a track between two locations relative to the one side of the patient support device;
    an IV pole having one end engaging the guide to permit the IV pole to move between the two locations; and
    the pole support further having a receptacle for supporting the IV pole in a generally vertical position at each of the two locations.

14. A patient support comprising:
    patient support structure;
    an IV pole;
    a base connected to the patient support structure for supporting the IV pole in a generally vertical position at two locations;
    a guide connected to the base to provide a track between the two locations relative to the base; and
    a member connected to the IV pole for engaging the guide to cause the IV pole to follow the track in moving between the two locations.

15. The patient support of claim 14 wherein the base includes a pole locking bracket at each of the two locations for supporting the IV pole in, selected generally vertical and generally horizontal positions.

16. An IV pole assembly movable to at least two locations comprising:
    an IV pole;
    a base for supporting the IV pole in a generally vertical position at each of the two locations;
    a guide connected to the base to provide a track between two locations relative to the base; and
    means connected to the IV pole for engaging the guide to permit the IV pole to move between the two locations.

17. The IV pole assembly of claim 16 wherein the base includes means for supporting the IV pole in a generally horizontal position.

18. A patient support comprising:
    a patient support structure;
    a pair of mounting brackets connected to the patient support structure at two locations;
    two pair of generally horizontal parallel rails extending substantially between two locations, the two pair of parallel rails forming guided paths between the two locations;

a pair of U-shaped pole locking brackets connected to the mounting brackets such that open sides of the U-shaped pole brackets face inwardly toward each other, each of the U-shaped pole locking brackets having generally horizontal first slots in opposed sides of each of the U-shaped pole locking brackets and each of the U-shaped pole locking brackets being connected to ends of the two pair of parallel rails so that first ends of each of the first slots are contiguous with and form extensions of the guided paths;

an IV pole;

a pole locking block connected proximate one end of the IV pole and slidably engagable in the U-shaped pole locking brackets, the pole locking block having
- a pair of first pins extending from opposite sides of the pole locking block and engagable with the first slots, thereby permitting the IV pole and pole locking block to slide in the first slots and the guided paths between the U-shaped pole locking brackets at the two locations, and
- a pair of second pins;

each pair of pole locking brackets including a pair of generally vertical second slots located at an opposite end of each of the first slots and intersecting each of the first slots to extend slightly above and below the first slots, the pair of second slots having upper ends and tapered lower ends, the pair of second slots receiving the pair of first pins in the tapered lower ends to lock the IV pole in a generally vertical position, and the pair of second slots receiving the pair of second pins in the upper ends to lock the IV pole in a generally horizontal position; and the pair of pole locking brackets including
- a pair of first notches on peripheral edges of the open sides for receiving the pair of second pins to further support the IV pole in the generally vertical position, and
- a pair of second notches on peripheral edges of the open sides and displaced below the pair of first notches for receiving the pair of second pins to further support the IV pole in its generally horizontal position.

* * * * *